United States Patent [19]

Guindon

[11] Patent Number: 5,314,914
[45] Date of Patent: May 24, 1994

[54] METHODS AND COMPOSITIONS FOR COMBATTING HERPES VIRUSES

[75] Inventor: Yvan Guindon, Montreal, Canada

[73] Assignee: BioMega/Boehringer Ingelheim Research Inc., Laval, Canada

[21] Appl. No.: 838,127

[22] Filed: Feb. 19, 1992

Related U.S. Application Data

[63] Continuation of Ser. No. 425,522, Oct. 23, 1989, abandoned.

[30] Foreign Application Priority Data

Oct. 27, 1988 [CA] Canada .................................. 581456

[51] Int. Cl.$^5$ ............................................. A61K 31/275
[52] U.S. Cl. .................................... 514/520; 514/522; 514/621; 514/675; 514/629; 514/630; 514/681
[58] Field of Search ............... 514/520, 522, 621, 625, 514/629, 630, 681

Primary Examiner—Frederick E. Waddell
Assistant Examiner—Russell Travers
Attorney, Agent, or Firm—D. E. Frankhouser; A. R. Stempel; M-E. M. Timbers

[57] ABSTRACT

A group of known naphthoquinone derivatives have been found to be useful for preventing or relieving herpes viral infections.

5 Claims, 1 Drawing Sheet

METHODS AND COMPOSITIONS FOR COMBATTING HERPES VIRUSES

This is a continuation of application Ser. No. 425,522, filed Oct. 23, 1989, now abandoned.

FIELD OF THE INVENTION

This invention relates to a method of preventing or relieving herpes viral infections in a mammal by administering thereto certain naphthoquinone derivatives. The invention also relates to a cosmetic formulation of the naphthoquinone derivatives and to the use of the formulation to prevent the outbreak of herpetic lesions of the skin.

BACKGROUND OF THE INVENTION

Since time immemorial, herpes viral infections have been a scourge of mankind and many important domestic animals. The herpes family of virus includes herpes simplex virus (types 1 and 2) responsible for cold sores and genital lesions, respectively; varicella zoster virus which causes chicken pox and shingles; and the Epstein-Barr virus which causes infectious mononucleosis. Although some significant advances have been made in the last decade in antiviral therapy, the need for effective, safe therapeutic agents for treating herpes viral infections continues to exist. For a recent review of current therapeutic agents in this area, see M. C. Nahata, "Antiviral Drugs: Pharmacokinetics, Adverse Effects and Therapeutic Use", J. Pharm. Technol., 3, 100 (1987).

It has now been found that a group of naphthoquinone derivatives, having a wide margin of safety, are useful for combatting herpes viral infections. The naphthoquinone derivatives are known having been cribed previously as antipsoriatic agents, see G. H. Jones and J. Young, U.S. Pat. No. 4,229,478, issued Oct. 21, 1980 and G. H. Jones et al., J. Med. Chem., 29, 1504 (1986).

Accordingly, the present invention provides a well tolerated and effective means for preventing or relieving herpes viral infections.

The association of antiviral activity with the above-noted naphthoquinone derivatives is an unusual finding. On a structural basis, it represents a departure from the chemical structures of compounds usually associated with antiviral activity, such as purine and pyrimidine nucleosides, 1-adamatanamine, particular interferons, etc. Two naphthalene derivatives, nevertheless, have previously been reported to have antiviral properties. The two naphthalene derivatives are 1,2,3,4-naphthalenetetrone, M. Y. Kraft et al., UK patent 1,243,401, Aug. 18, 1971, and 6-bromo-1,2-naphthalenedione, L. F. Stebaeva et al., Farmakol. Toksikol. (Moscow), 43, 609 (1980); Chem. Abstr., 93, 179724j (1980). The naphthoquinone derivatives of the present application are distinguished readily from the latter two naphthalene derivatives by marked structural differences arising from the substituents on their bicyclic structures.

SUMMARY OF THE INVENTION

Disclosed herein is a method for preventing or relieving herpes viral infections in a mammal. The method comprises administering to the mammal an anti-herpes virally effective amount of a naphthoquinone derivative of formula 1

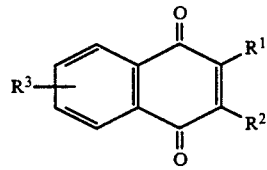

wherein $R^1$ and $R^2$ are the same or different and are hydrogen, alkoxy (1 to 18C) or acylamino (1–18C), and $R^3$ is selected from the group of hydrogen, halo, cyano, alkoxy and the group $-S(O)_nR$ wherein R is selected from the group of alkyl optionally substituted with phenyl or a substituted phenyl, the substituents selected from lower alkyl, lower alkoxy, halo, lower acyl, lower acyloxy, phenyl optionally substituted with halo, dihalo, cyano, nitro, amino, lower acylamino, di(lower acyl)amino, alkoxy or alkyl, heterocyclic aryl optionally substituted with halo, cyano, lower alkyl or lower alkoxy and the therapeutically acceptable salts of said heterocyclic aryl, and n is the integer 0, 1 or 2; with the proviso that $R^1$ and $R^2$ are not both hydrogen.

A preferred group of the derivatives for effecting the method of this invention is represented by formula 1 wherein $R^1$ and $R^2$ are the same or different and are hydrogen, hydroxy or alkoxy and $R^3$ is hydrogen, halo, cyano or alkoxy, with the proviso that $R^1$ and $R^2$ are not both hydrogen.

A more preferred group of the derivatives for effecting the method is represented by formula 1 wherein $R^1$ and $R^2$ are the same and are hydroxy, methoxy, ethoxy, propoxy, butoxy, 2-methylpropoxy, or 1,1-dimethylethoxy, and $R^3$ is a substituent at the 5 or 6 position of the naphthoquinone ring system, the substituent being selected from the group consisting of bromo, chloro, fluoro, cyano, phenylthio, methylthio, methoxy, ethoxy, propoxy, 1-methylethoxy, butoxy, 2-methylpropyl, acetyl and benzoyl.

A most preferred group of the derivatives for effecting the method is represented by formula 1 wherein $R^1$ and $R^2$ are the same and are lower alkoxy, and $R^3$ is a substituent at the 6 position of the naphthoquinone system, the substituent being selected from the group consisting of bromo, chloro, fluoro, cyano, methoxy, ethoxy, propoxy, 1-methylethoxy, butoxy and 2-methylpropoxy.

In another aspect of the present invention, a cosmetic composition is provided. The cosmetic composition comprises a naphthoquinone derivative of formula 1, or a therapeutically acceptable salt thereof, and a physiologically acceptable carrier. The cosmetic composition is used to prevent the outbreak of herpetic lesions of the skin.

DETAILED DESCRIPTION OF THE INVENTION

Figure 1:
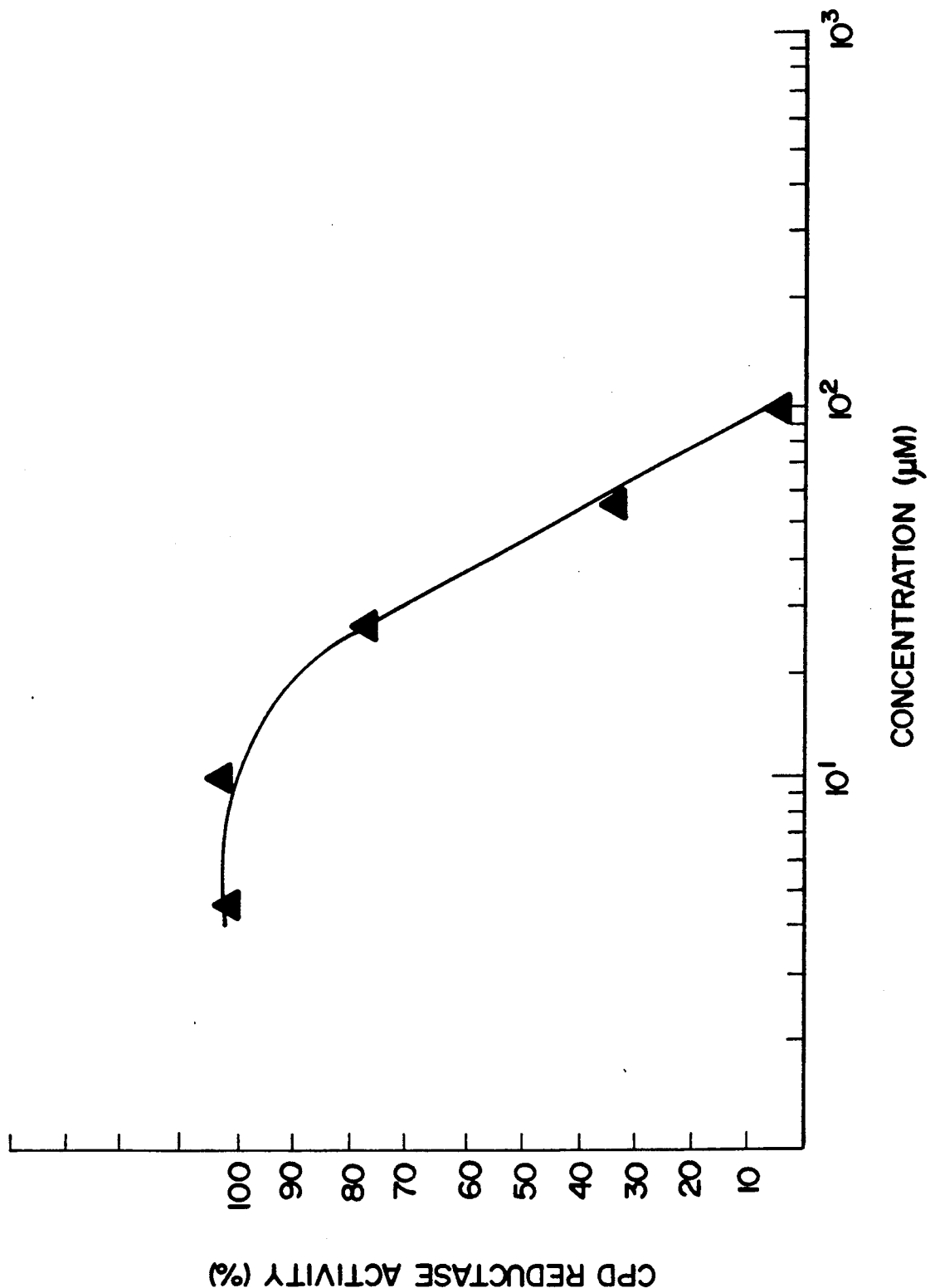
FIG. 1 shows the progressively greater inhibitory effect of increasing concentrations of the naphthoquinone derivative of formula 1 in which $R^1$ and $R^2$ are each methoxy and $R^3$ is 6-chloro on herpes simplex virus (type 1) ribonucleotide reductase activity.

For convenience, the naphthoquinone derivatives of formula 1 are designated hereafter simply as "naphthoquinones".

The term "alkyl" as used herein means an alkyl radical containing one to eighteen carbon atoms and includes straight chain as well as branched chain radicals. Illustrative of such radicals are methyl, ethyl, propyl, 1-methylethyl, heptyl, nonyl and pentadecyl. The term "lower alkyl" means an alkyl radical containing one to four carbon atoms and includes straight chain and branched chain alkyl radicals.

The term "alkoxy" means a straight or branched chain aliphatic group of one to eighteen carbon atoms having bonded thereto an oxygen moiety. Examples of "alkoxy" are methoxy, ethoxy, propoxy, 1-methylethoxy, butoxy, nonyloxy and dodecyloxy. The term "lower alkoxy" means a straight and branched chain alkoxy radicals containing one to four carbon atoms.

The term "halo" refers to fluoro, chloro and bromo. The term "cyano" refers to the group —CN. The term "amino" refers to the group —$NH_2$.

The term "lower acyl" when used alone or in combination refers to the group $R^4C(O)$— wherein $R^4$ is a lower alkyl group of one to three carbon atoms or an optionally substituted phenyl group. Examples of "lower acyl" are acetyl, propanoyl, butanoyl and benzoyl.

The term "heterocyclic aryl" is defined as those cyclic aromatic compounds having 3 to 9 ring carbon atoms and having one or two heteroatoms in the ring selected from the group consisting of nitrogen, oxygen and sulfur. Example of such include the groups thiapyranyl, benzothiapyranyl, furyl, pyrrolyl, imidazolyl, pyrazolyl, pyridinyl, pyrimidinyl, indolyl, quinolinyl, indazolyl and the like. These heterocyclic aryls may be optionally substituted with halo, lower alkyl, cyano and lower alkoxy.

The term "therapeutically acceptable acid addition salts", as used in the case of the various $R^3$ radicals containing basic, heterocyclic aryl substituents, means those non-toxic therapeutically acceptable acid additional salts which do not adversely affect the pharmaceutical properties of the parent compounds. With respect to these addition salts, suitable inorganic anions included, for example, chloride, bromide, iodide, sulfate, phosphate, nitrate, and the like. Suitable organic anions include, for example, acetate, benzoate, lactate, propionate, butyrate, valerate, tartrate, maleate, fumarate, citrate, succinate, tosylate, ascorbate, nicotinate, adipate and gluconate.

The term "physiologically acceptable carrier" as used herein means an acceptable cosmetic vehicle suitable for topical application to the skin of one or more non-toxic excipients which do not react with, or reduced the effectiveness of, the active ingredient contained therein.

The term "effective amount" means a predetermined antiviral amount of the antiviral agent which is effective against the viral organism in vivo.

The naphthoquinones of formula 1 can be prepared by previously disclosed procedures described by G. H. Jones and J. Young in U.S. Pat. No. 4,229,478 and by G. H. Jones et al. in the J. Med. Chem. publication, cited hereinabove. The disclosures of the U.S. patent and the J. Med. Chem. publication are herein incorporated by reference.

The antiviral activity of the naphthoquinones of formula 1 can be demonstrated by biochemical, microbiological and biological procedures showing the inhibitory effect of the compounds on the replication of herpes simplex viruses, types 1 and 2 (HSV-1 and HSV-2); and other herpes viruses, for example, varicella zoster virus (VZV), Epstein Barr virus (EBV), equine herpes virus (EHV) and pseudorabies virus (PRV).

Noteworthy is the fact that all of the aforementioned viruses are dependent on their own ribonucleotide reductase to synthesize deoxyribonucleotides for their replication. Although this fact may not be directly linked with the antiviral activity found for the present naphthoquinones, the latter compounds have been shown so far to have antiviral properties against all viruses dependent on ribonucleotide reductase to synthesis DNA for their replication.

In example 1 hereinafter, the inhibitory effect of an exemplary naphthoquinone is noted with respect to the specific inhibition of herpes ribonucleotide reductase. Noteworthy, in the connection with the specific inhibition of herpes ribonucleotide reductase, is the absence of such an effect on cellular ribonucleotide reductase activity required for normal cell replication.

A method for demonstrating the therapeutic effect of the naphthoquinones is the guinea pig model for cutaneous herpes simplex viral infections; see S. Alenius and B. Oberg, Archives of Virology, 58,277 (1978).

When a naphthoquinone of this invention, or one of its therapeutically acceptable salts, is employed as an antiviral agent, it is administered topically or systemically to warm-blooded animals, e.g. humans, pigs or horses, in a vehicle comprising one or more pharmaceutically acceptable carriers, the proportion of which is determined by the solubility and chemical nature of the naphthoquinone, chosen route of administration and standard biological practice. For topical administration, the naphthoquinone can be formulated in pharmaceutically accepted vehicles containing 0.1 to 10 percent, preferably 0.5 to 5 percent, of the active agent. Such formulations can be in the form of a solution, cream or lotion.

For systemic administration, the naphthoquinone of formula 1 is administered by either intravenous, subcutaneous or intramuscular injection, in compositions with pharmaceutically acceptable vehicles or carriers. For administration by injection, it is preferred to use the compound in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described by G. H. Jones et al. in the previously noted U.S. patent, or they can be found in standard pharmaceutical texts, e.g. in "Remington's Pharmaceutical Sciences", 16th ed, Mack Publishing Company, Easton, Pa., 1980.

The dosage of the naphthoquinone will vary with the form of administration and the particular active agent chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the naphthoquinone is most desirably administered at a concentration level that will generally afford antivirally effective results without causing any harmful or deleterious side effects.

With reference to topical application, the naphthoquinone is administered cutaneously in a suitable topical formulation to the infected area of the body e.g. the skin or part of the oral or genital cavity, in an amount sufficient to cover the infected area. The treatment should be repeated, for example, every four to six hours until lesions heal. Healing results usually within 3 to 4 days. No contraindications have been observed.

With reference to systemic administration, the naphthalene of formula 1 is administered at a dosage of 10 mcg to 1000 mcg per kilogram of body weight per day, although the aforementioned variations will occur. However, a dosage level that is in the range of from about 50 mcg to 500 mcg per kilogram of body weight per day is most desirably employed in order to achieve effective results.

Although the formulation disclosed hereinabove are effective and relatively safe medications for treating herpes viral infections, the possible concurrent administration of these formulations with other antiviral medications or agents to obtain beneficial results is not excluded. Such other antiviral medications or agents include acyclovir and antiviral surface active agents or antiviral interferons such as those disclosed by S. S. Asculai and F. Rapp in U.S. Pat. No. 4,507,281, Mar. 26, 1985.

Another aspect of this invention comprises a cosmetic composition comprising a herpes viral prophylactic amount of the naphthoquinone of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of herpetic lesions of the skin. The formulation can be applied nightly to susceptible areas of the skin. Generally, the cosmetic composition contains less of the naphthoquinone than corresponding pharmaceutical compositions for topical application. A preferred range of the amount of the naphthoquinone in the cosmetic composition is 0.01 to 0.2 percent by weight.

The following example further illustrates this invention.

EXAMPLE 1

Specific Inhibition of HSV-1 Ribonucleotide Reductase by 6-Chloro-2,3-dimethoxy-1,4-naphthalenedione (1: $R^1$ and $R^2 = CH_3O$ and $R^3 = 6-Cl$)

HSV-1 ribonucleotide reductase (partially purified) was obtained from quiescent BHK-21/C13 cells infected with strain F HSV-1 virus at 10 plague-forming units/cell as described by E. A. Cohen et al., J. Gen. Virol., 66, 733 (1985).

Hamster 96-V-2(600) ribonucleotide reductase (partially purified) was obtained from an overproducing strain of a Chinese hamster lung cell line as described by W. H. Lewis and P. R. Srinivasan, Mol. Cell Biol., 3, 1053 (1983).

Samples of the HSV-1 ribonucleotide reductase (65 μg with a specific activity of 26 units per mg) were mixed with increasing concentrations of the test compound, i.e. the naphthalene noted in the title of this example, in a series of tubes. Ribonucleotide reductase activity was assayed by monitoring the reduction of cytidine diphosphate (CDP) as described by Cohen et al., supra. The standard reaction mixture, in a final volume of 60 μl, contained: 50 mM, N-2-hydroxyethylpiperazine-N'-2-ethanesulfonic acid (pH 7.8); 4 mM NaF, 30 mM DL-dithiothreitol (DTT); 1 mM bacitracin, 54 μM CDP and 0.25 μCi of [$^3$H]CDP. After 30 minutes of incubation at 37° C., the reaction was stopped by immersing the tube in boiling water for 4 minutes. The precipitate was removed by centrifugation. Nucleotides in the supernatant were converted to nucleosides by enzymatic hydrolysis. The deoxyribonucleosides were subsequently separated from the ribonucleosides by ascending polyethyleneimine-celulose chromatography. One unit of ribonucleotide reductase is defined as the amount of enzyme generating 1 nmol of dCDP per hour under standard conditions. A control experiment (without the test compound) was run simultaneously. The results, shown in FIGURE 1, are expressed as a percentage of the activity obtained in the controls.

As shown in FIG. 1, a fifty percent reduction of the HSV-1 ribonucleotide reductase activity was observed with 40 μM of the title compound, i.e. $IC_{50} = 40$ μM. In a similar experiment wherein HSV-1 ribonucleotide reductase was replaced with hamster 96-V-2(600) ribonucleotide reductase (40 μg with a specific activity = 38 units per mg) in the presence of adenosine triphosphate (4 mM) and magnesium chloride (11.5 mM), the $IC_{50}$ for the test compound was shown to be greater than 250 μM. Hence, the selective inhibition by the test compound of the viral ribonucleotide reductase over the cellular ribonucleotide reductase was demonstrated.

In the same manner, selective inhibition of HSV-1 ribonucleotide reductase activity is shown for 2,3-dimethoxy-1,4-naphthalenedione, 2,3,6-trimethoxy-1,4-naphthalenedione, 6-cyano-2,3-dimethoxy-1,4-naphthalenedione, 6-chloro-2,3-diethoxy-1,4-naphthalenedione and 6-chloro-2,3-dipropoxy-1,4-naphthalenedione.

The embodiments of the invention for which an exclusive property or privilege is claimed are defined as follows:

1. A method for relieving herpes viral infections in a mammal which comprises administering to the mammal an effective amount of a compound of the formula

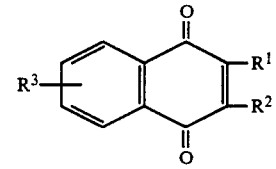

wherein $R^1$ and $R^2$ are the same and are methoxy, ethoxy, propoxy, butoxy, 2-methylpropoxy or 1,1-dimethylethoxy and $R^3$ is a substituent at the 5 or 6 position of the naphthoquinone ring system, the substituent being selected from the group consisting of bromo, chloro, fluoro, cyano, phenylthio, methylthio, methoxy, ethoxy, propoxy, 1-methylethoxy, butoxy, 2-methylpropyl, acetyl and benzoyl.

2. The method of claim 1 wherein $R^3$ is a substituent at the 6 position of the naphthoquinone system, selected from the group consisting of bromo, chloro, fluoro, cyano, methoxy, ethoxy, propoxy, 1-methylethoxy, butoxy and 2-methylpropoxy.

3. The method of claim 2 wherein $R^3$ is a substituent selected from the group consisting of bromo, chloro, fluoro and cyano.

4. The method of claim 2 wherein the compound is 6-chloro-2,3-dimethoxy-1,4-naphthalenedione, 2,3,6-trimethoxy-1,4-naphthalenedione, 6-cyano-2,3-dimethoxy-1,4-naphthalenedione, 6-chloro-2,3-diethoxy-1,4-naphthalenedione, or 6-chloro-2,3-dipropoxy-1,4-naphthalenedione.

5. A method for relieving herpes viral infections in a mammal which comprises administering to the mammal an effective amount of 2,3-dimethoxy-1,4-naphthalenedione.

* * * * *